United States Patent [19]
Askin et al.

[11] Patent Number: 5,169,952
[45] Date of Patent: Dec. 8, 1992

[54] STEREOSELECTIVE PRODUCTION OF HYDROXYAMIDE COMPOUNDS FROM CHIRAL α-AMINO EPOXIDES

[75] Inventors: David Askin, Warren; Ralph Volante, East Windsor; Michael Wallace, Matawan; Ichiro Shinkai, Westfield, all of N.J.

[73] Assignee: Merck & Co., Inc., Rahway, N.J.

[21] Appl. No.: 724,617

[22] Filed: Jul. 2, 1991

[51] Int. Cl.$^5$ .................. C07C 271/20; C07D 263/52; C07D 295/104
[52] U.S. Cl. ................... 544/137; 548/217; 560/28; 544/165
[58] Field of Search ............... 548/217; 544/137, 165; 560/28

[56] References Cited
PUBLICATIONS

Marshall et al, *Journal of Organic Chemistry*, vol. 50 (1985) pp. 1602–1606.

Primary Examiner—Robert W. Ramsuer
Attorney, Agent, or Firm—Charles M. Caruso; Roy D. Meredith; Carol S. Quagliato

[57] ABSTRACT

An efficient process for stereoselective preparation of a medicinally significant hydroxyamide compound of structural formula:

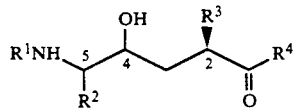

comprises the addition of metalated amide enolates to chiral α-amino metalated epoxides. The hydroxyamide reaction products are useful as inhibitors of the HIV protease or of renin, or as intermediates in the preparation of inhibitors of the HIV protease or renin.

10 Claims, No Drawings

STEREOSELECTIVE PRODUCTION OF HYDROXYAMIDE COMPOUNDS FROM CHIRAL α-AMINO EPOXIDES

BACKGROUND OF THE INVENTION

The present invention concerns the diastereoselective synthesis of hydroxyethylene dipeptide isosteres III by a novel route which involves the addition of the amide II to the epoxide I by treatment with strong base at low temperatures, as shown below in Scheme I.

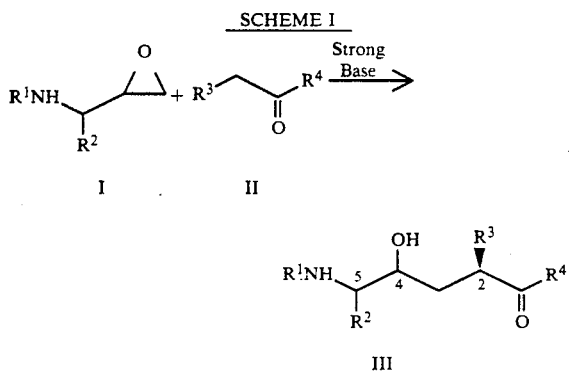

SCHEME I

Hydroxyethylene dipeptide isosteres are medicinally important enzyme (renin and HIV protease) inhibitors. In particular, 2 R, 4 S, 5 S diastereomeric hydroxyamide isosteres have been pursued and synthesized as intermediates in the preparation of such enzyme inhibitors, as well as being end-product inhibitors themselves. See, e.g., Vacca, J. P., et al., *J. Med. Chem.*, 34:1228 (1991).

In the past, entry into the the synthesis of hydroxyethylene dipeptide isosteres involved alkylation of a lactone, derived from an aldehyde, DeCamp, A. E., et al., *Tetrahedron Lett.*, 32: 1867 (1991), with various aryl halides to afford the trans-alkylated lactone products. Evans, B. E., et al., *J. Org. Chem.*, 50:4615 (1985); Fray, A. H., et al., *J. Org. Chem.*, 51:4828 (1986).

In the prior art, a four step coupling procedure is necessary to effect amide bond formation from the alkylated lactone for the synthesis of the isosteres of structure III, which is a major problem with this route. The alkylated lactone is saponified to afford an intermediate hydroxy-acid which is then protected at the hydroxyl group to afford the carboxylic acid intermediate. The carboxylic acid intermediate is then coupled with an amine to afford the hydroxy protected isostere which is finally deprotected to afford the isostere III. In addition to being lengthy, the process requires expensive reagents to activate the carboxylic acid, is operationally difficult on a large scale and results in some recovery of the alkylated intermediate lactone after the amide bond formation step. Thus, a new route to the hydroxyethylene dipeptide isosteres that does not involve the lengthy and ineffecient conversion of an alkylated lactone to the desired isostere III would be superior to existing methodology.

The work of Marshall, et al., *J. Org. Chem.*, 50:1602 (1985), has shown that epoxides bearing α-(metalloalkoxide) groups are much more reactive than the corresponding epoxides bearing α-ether groups. However, no examples exist of the reaction of epoxides bearing α-(metallo-amino) or α-[metallo-(N-t-butoxycarbonylamino)] groups with metalated amide enolates.

Experiments involving the reaction of the metalated amide enolate derived from compound II in Scheme I with simple unsubstituted epoxides show that a substantial rate acceleration is gained via epoxide activation by the α-metalated amino group.

Although metalated chiral amide enolates have been previously used to form 2-alkyl-4-hydroxycarboxamide products by reaction with chiral epoxides [Askin, D., et al., *Tetrahedron Lett.*, 29:4245 (1988)], metalated chiral amide enolates have not previously been used to make hydroxyethylene dipeptide isosteres III by reaction with α-N-metalated chiral epoxides.

The present invention has several advantages over the prior art for making medicinally important intermediates and end-product compounds useful for the treatment of serious diseases. Most importantly, the novel process of the invention provides a rapid entry into hydroxyethylene dipeptide isosteres by circumventing the problematic four-step coupling/amidation sequence. Thus, the invention is a more economical, operationally practical and efficient process for the construction of hydroxy-ethylene dipeptide isosteres than previous processes. This invention provides a direct, high yielding, stereoselective route to hydroxyamide compounds useful in the preparation of diastereomeric compounds having the ability to inhibit certain proteolytic enzymes, including renin and the protease of human immunodeficiency virus (HIV).

SUMMARY OF THE INVENTION

The novel process of the invention is summarized according to SCHEME I:

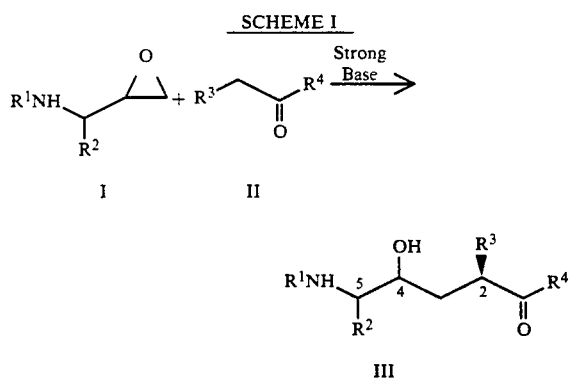

SCHEME I whereby an epoxide of structural formula I and an amide of structural formula II are reacted by treating I and II with strong base at low temperatures. The strong base effects metalation of the amino group of I and metalation of the amide II at the position α-to the carbonyl group to afford the reactive metal amide enolate which then effects ring opening of the metalated epoxide at the terminal position to afford the product III. A new center of asymmetry is created in the product III at the 2-position. The reaction may be run in one or two steps. Compounds comprehended by III are useful in the preparation of inhibitors of proteolytic enzymes, especially of the HIV protease, and of renin, and some of the compounds of formula III are themselves useful inhibitors of the HIV protease.

DETAILED DESCRIPTION OF THE INVENTION

This invention provides a direct, high yielding, stereoselective route to hydroxyamide compounds via metallo-enolate methodology. The process is represented in Scheme I as the addition of the amide II to a chiral epoxide I by treatment with strong base at low temperature to yield the hydroxyamide III. Nearly exclusive formation of a single diastereomer of III results from this reaction scheme:

SCHEME I

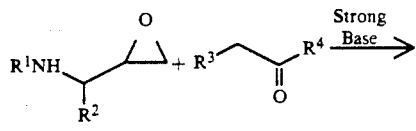

I     II

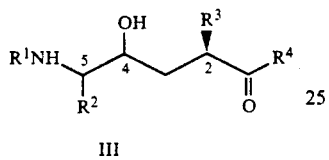

III at low temperatures in an etherial solvent, wherein:

$R^1$ is:
  a) t-Boc, Aoc, Adc, Mcb, Mch, Cbz, Alloc, or Fmoc,
  b) benzyl,
  c) lower alkyl,
  d) $CH_3O(CH_2CH_2O)_nCO-$, wherein n is from 1 to 10,
  e) tetrahydrofuranyloxy—CO—, or
  f) R—CO—, wherein R is an amino acid;

$R^2$ is:
  a) —H,
  b) benzyl,
  c) cyclohexyl—$CH_2$—,
  d) isobutyl,
  e) benzyl—O—benzyl—,
  f) cinnamyl—, or
  g) parahydroxybenzyl;

$R^3$ is:
  a) —H,
  b) lower alkyl,
  c) phenyl,
  d) benzyl,
  e) —$CH_2$—phenyl—O—$R^5$, or
  f) —$CH_2$—CH=CH—phenyl—O—$R^5$;

$R^4$ is:
  a)

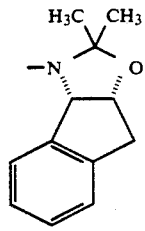

b)

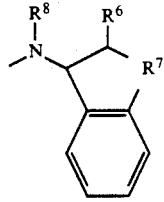

wherein:
$R^6$ is —H, or —OH;
$R^7$ is —$CH_2$—O—, or

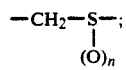

$n = 0$, 1, or 2;

c)

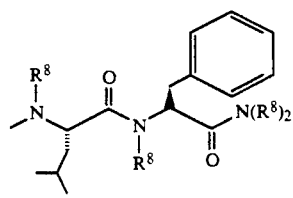

d)

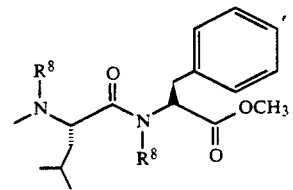

e)

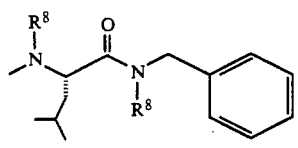

f)

g)

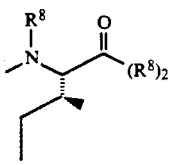

or h)

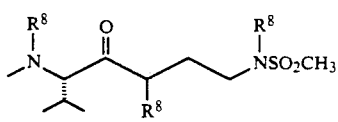

$R^5$ is:
a) —H
b) benzyl,
c) —CH$_2$CH$_2$—OH, or
d)

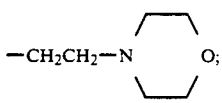

$R^8$ is a removable protecting group selected from among:
a) t-Boc, Aoc, Adc, Mcb, Mch, Cbz, Alloc, or Fmoc, or
b) benzyl; and $R^9$ is:
a) lower alkyl, or
b) benzyl.

The strong base must be a metal-containing base. The strong base may or may not be in an inert anhydrous organic solvent, such as, e.g., cyclic or acyclic hydrocarbons including hexane, pentane, cyclohexane, etc. Suitable strong bases include n-butyllithium (n-BuLi), s-BuLi, t-BuLi, potassium tert-butoxide, lithium diisopropylamide (LDA), lithium isopropylcyclohexylamide, lithium pyrrolidide, lithium tetramethylpiperidide, phenyllithium, isopropylmagnesium chloride, isobutylmagnesium chloride, and other similar strong bases known in the art. Preferred strong bases are n-BuLi, s-BuLi, isopropyl magnesium chloride and LDA, with n-BuLi and isopropyl magnesium chloride being most preferred.

The strong base employed in Scheme I effects metalation of the amino group of epoxide I and metalation of the amide II at the position α to the carbonyl group to afford the reactive metal amide enolate which then effects ring opening of the metalated epoxide at the terminal position to afford the product III. A new center of asymmetry is created in the product isostere III at the 2-position. A surprising finding in this invention is that for certain chiral epoxides I and chiral amides II, nearly exclusive formation of a single diastereomeric isostere III results. Thus, a key aspect of the invention concerns the high selectivity in the formation of the 2-stereocenter of III (with the desired stereochemistry) in the condensation of the metalated amide enolate derived from II (where $R^4$ may or may not possesses chirality) with electrophiles such as the metalated epoxide derived from I (i.e., where the —NH— of epoxide I=—N(metal)—).

The reaction of Scheme I is preferably run at a low temperature, for example ranging between about −82° C. and 0° C. To effect metalation of the epoxide I and amide II, the temperature range is maintained more preferably between about −82° C. and −65° C., and most preferably between about −80° C. and −75° C., and to effect the reaction of the metalated derivatives of I and II to form III, the temperature range is maintained more preferably between about −50° C. and −10° C., and most preferably between about −30° C. to −20° C.

The etherial solvents are any solvents suitable for use in Scheme I, including, e.g., tetrahydrofuran, 1,2-dimethoxyethane, di-ethyl ether and methyl-t-butyl ether, with tetrahydrofuran being preferred.

It is to be understood that the nitrogen protecting groups provided for in the definitions above may be removed to generate free amino compounds. Thus, the $R^8$ group, wherever it appears, may be removed according to methods known in the art. Furthermore, the cyclic-aminal protecting acetonide (also called isopropylidene), present in the definition of $R^4$ part (a), may similarly be removed.

As used herein, lower alkyl means straight or branched chain alkyls of one to five carbon atoms. When any one variable occurs more than one time in a molecule, its definition on each occurrence is independent of its definition at every other occurrence. Ph stands for phenyl, Bn for benzyl, and Et for ethyl. Aoc, t-Boc, etc., are amino or urethane protecting groups known in the art; t-Boc is preferred as it is easily removed under mild conditions. As used herein, the term amino acid encompasses all naturally ocurring amino acids.

The novel process of the present invention can be done in either one step or two steps. The two-step procedure involves the metalation of the epoxide I with a strong base at reduced temperatures, and the separate metalation of the amide II with the same or a different strong base at reduced temperatures, followed by addition of the metalated epoxide and the metalated amide enolate to produce the hydroxyamide product III. Alternatively, the epoxide and the amide can both be metalated and reacted in one step by addition of approximately 2 to 3 molar equivalents of a strong base to a solution containing about a 1:1 molar equivalent of both the epoxide I and the amide II to produce III.

In a preferred embodiment of the novel process, shown below in Scheme II, the chiral epoxide IV is metalated with a strong base, preferably isobutylmagnesium chloride, n-BuLi, s-BuLi, or LDA, and most preferably isobutylmagnesium chloride or n-BuLi, to produce the α-[metallo-(N-t-Boc-amino)]epoxide V, by treating IV with the strong base at low temperatures.

Addition of V to the metalated amide enolate derived from treatment of II with strong base at low temperatures provides VI almost exclusively as the 2 R, 4 S, 5 S diastereomer. The amide II is converted to the metalated amide enolate preferably by treatment with n-BuLi, s-BuLi or LDA, and most preferably with n-BuLi.

The 2 R, 3 S epoxide IV is prepared from commercially available amino acids or N-protected amino acids according to standard techniques well known in the art to one of ordinary skill such as, for example, the procedure disclosed in Luly, et al., *J. Org. Chem*, 52:1487 (1987).

The amide II is prepared, for example, from condensation of commercially available 3-phenylpropionic acid (also known as hydrocinnamic acid), substituted or unsubstituted on the phenyl ring, with an amine of formula H—$R^4$, where $R^4$ is as previously defined, and $R^4$ may or may not have protecting groups on it. H—$R^4$ is preferably (1 S, 2 R)cis-1-amino-2-indanol, which can be protected as the acetonide once the amide coupling is complete (see Example 2). (1 S, 2 R)-Cis-1-amino-2-indanol is prepared from commercially available indene according to standard techniques well known in the art to one of ordinary skill such as, for example, the procedures disclosed in Hassner, et al., *J. Org. Chem.*, 32:540 (1966), and resolved according to standard techniques well known in the art.

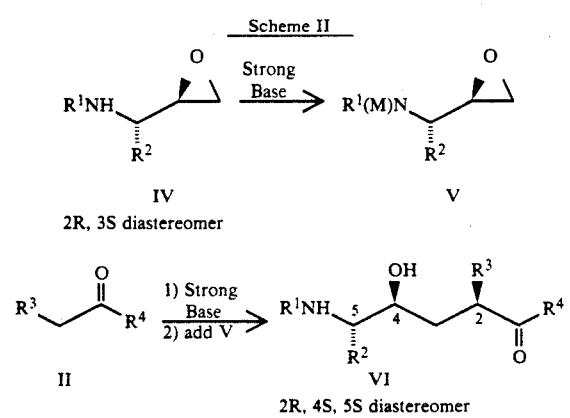

Scheme II

IV
2R, 3S diastereomer

V

II

VI
2R, 4S, 5S diastereomer wherein M represents the metal or metal group that corresponds to the metal or metal group contained in the strong base chosen for use with the epoxide IV in the procedure. For example, when n-BuLi is the strong base used to treat IV, M is Li; when isopropyl magnesium chloride is used, M is MgCl.

In another preferred embodiment of the novel process, shown below in Scheme III, approximately 1:1 molar equivalents of epoxide IV and amide II are combined in one pot with appropriate solvent and reacted by treatment with approximately 2 to 3 molar equivalents of strong base, preferably n-BuLi, s-BuLi, or LDA and most preferably n-BuLi, to form the corresponding α-metallo (N-t-Boc-amino) epoxide and metallated amide enolate. The reaction yields VI almost exclusively as the 2 R, 4 S, 5 S diastereomer.

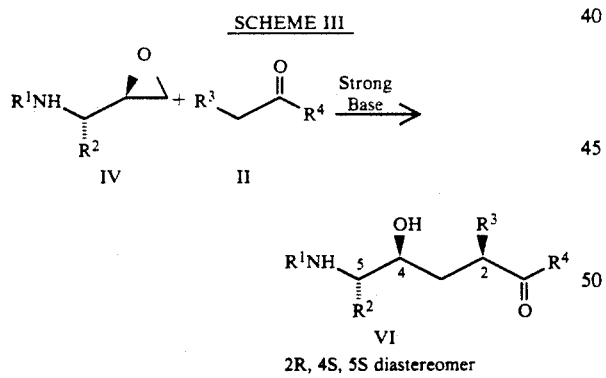

SCHEME III

IV    II

VI
2R, 4S, 5S diastereomer

The compounds produced by the novel process of this invention are useful as intermediates in the preparation of peptides having defined stereochemistry. Furthermore, compounds having in vitro or in vivo renin or HIV protease inhibitory activity may be prepared directly according to the disclosed process.

Thus, in another preferred embodiment of this invention, the following 2 R, 4 S, 5 S diastereomeric hydroxyamide compounds of structural formula X described in Table I, useful as inhibitors of the HIV protease, are prepared from the corresponding epoxide VII and amide VIII starting materials, also described in Table I. Each compound of Table I is prepared from reaction of the corresponding α-[metallo-(N-t-Boc-amino)]-epoxide with the corresponding metalated amide enolate according to either Scheme II or Scheme III, followed by deprotection of the novel intermediate IX to the amide and hydroxyl containing compound X (see Example 8).

TABLE I

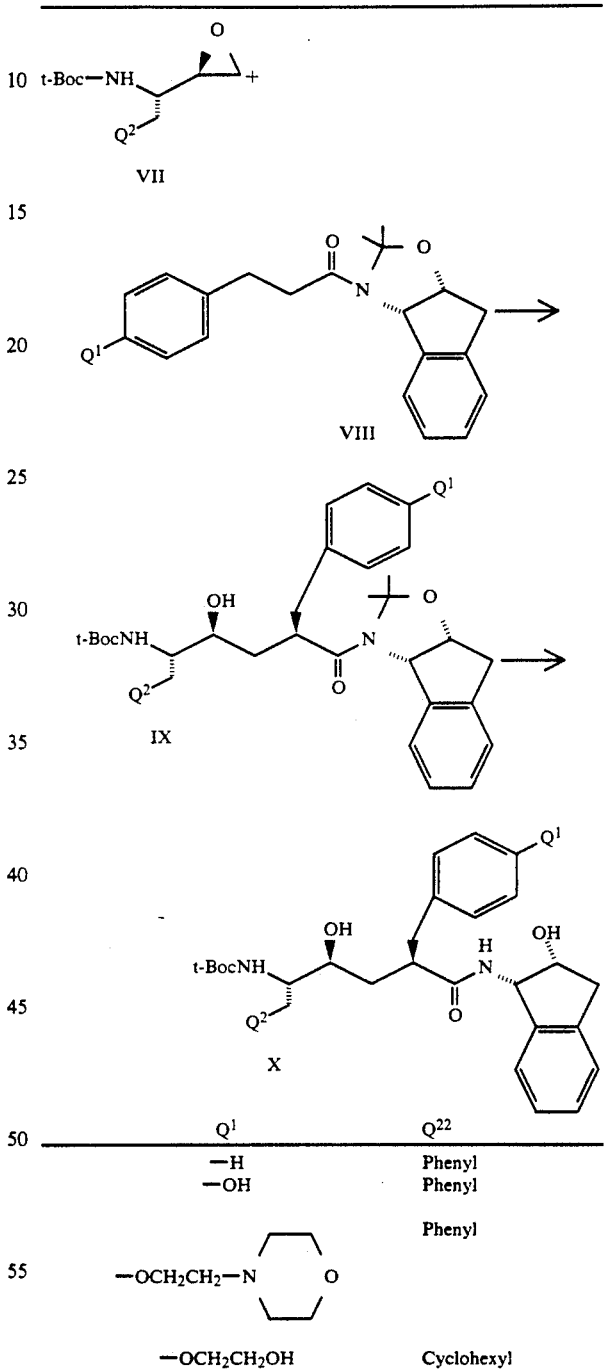

| $Q^1$ | $Q^{22}$ |
|---|---|
| —H | Phenyl |
| —OH | Phenyl |
| —OCH₂CH₂—N⟨O⟩ (morpholino) | Phenyl |
| —OCH₂CH₂OH | Cyclohexyl |

The novel process of this invention is useful to prepare diastereomeric compounds for in vitro testing as inhibitors of the HIV protease, renin, or other proteases of interest.

Furthermore, HIV protease or renin inhibitory compounds produced by this process may be administered to patients in need of such treatment in pharmaceutical compositions comprising a pharmaceutical carrier and

EXAMPLE 1

Preparation of Amide 4

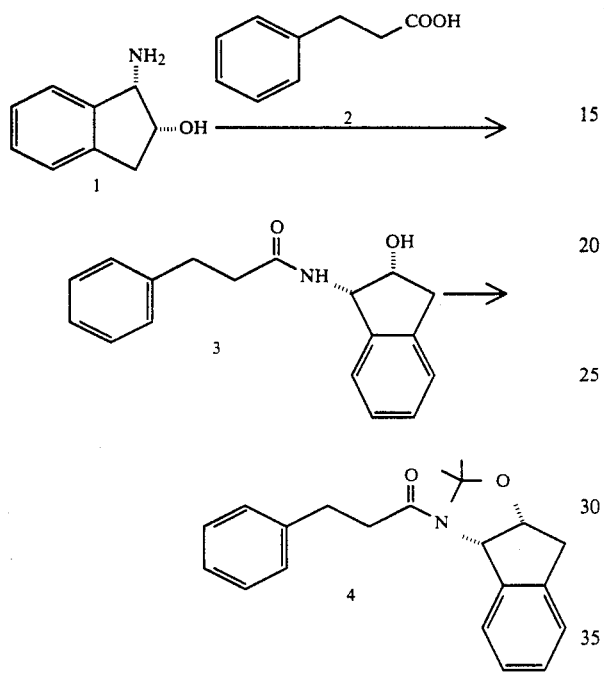

hydrocinnamic acid (2, 50.4 g, 0.336 mol) was dissolved in 400 mL of dry THF and cooled to 0° C. Triethylamine (49.0 mL, 0.352 mol) was added followed by pivaloyl chloride (41.3 mL, 0.335 mol) which was added over a 25 min period. The mixture was aged at 0° C. for 1 h. The amino-alcohol 1 (50.0 g, 0.335 mol) (prepared according to Hassner, A. et al., *J. Org. Chem.* 1966, 32:540) was then dissolved in 750 mL THF and added to the 0° C. reaction mixture over a 1 h period. The mixture was then warmed to 25° C. and aged for 2.5 h. The reaction was partitioned with 1000 mL ethyl acetate and 500 mL water. The layers were separated and the aqueous layer extracted once with 500 mL of ethyl acetate. The combined organic layers were washed with 400 mL water, 400 mL aqueous sodium bicarbonate, 400 mL saturated sodium sulfate and dried ($MgSO_4$). The dried organic phase was concentrated in vacuo to afford the crude amide 3 which was slurried in 900 mL of $CH_2Cl_2$ at 25° C. To this suspension was added 2-methoxypropene (38.8 mL, 0.405 mol) followed by pyridinium paratoluenesulfonate (8.4 g, 34 mmol). The resulting pale yellow solution was aged at 25° C. for 5.5 h, then poured into 600 mL of saturated aqueous sodium bicarbonate. The layers were separated and the aqueous layer was extracted with 250 mL of $CH_2Cl_2$. The combined organic phase was washed with 100 mL saturated aqueous sodium bicarbonate, 100 mL water, and dried over $MgSO_4$. The volatiles were removed in vacuo to afford 82 g of crude product that was dissolved in 50 mL of THF at 50° C. and cooled to 25° C. Hexane (275 mL) was then added over 45 min to the stirred slurry which was then cooled to 0° C. and filtered. The product was washed with 50 mL of cold hexane and dried at high vacuum to afford 79.25 g (74% overall) of the acetonide amide derivative 4 as a white solid.

$^{13}C$ NMR (75.5 MHz, $CDCl_3$, major rotamer) $\delta_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

EXAMPLE 2

Preparation of phenol-amide 8

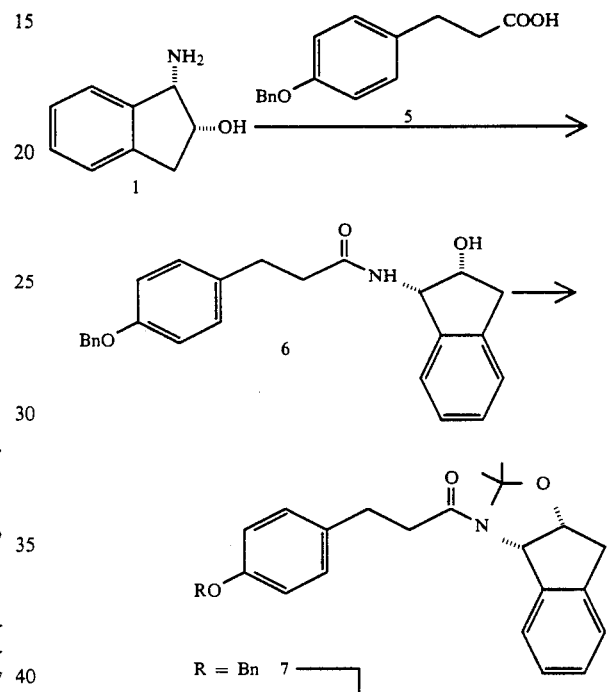

To a solution of 3-(4-Benzyloxy-phenyl)propionic acid (5, 10.1 g, 39.4 mmol) in 260 mL sieve dried DMF at 25° C. was added the amino-alcohol 1 (5.88 g, 39.4 mmol), HOBT-hydrate (6.39 g, 47.3 mmol), EDC (11.3 g, 59.1 mmol) and 1-methyl-piperidine (7.18 mL, 59.1 mmol). The resulting mixture was aged at 25° C. for 21 h, then the volatiles were removed by concentration in vacuo. The crude residue was diluted with 250 mL of ethyl acetate and washed with 100 mL of water. The aqueous layer was back-extracted with ethyl acetate (2×100 mL), and the combined organic layer was washed with 100 mL 10% citric acid, 100 mL of water, 100 mL of saturated aqueous $NaHCO_3$, 100 mL of saturated aqueous NaCl. The organic phase was dried over $MgSO_4$ and concentrated in vacuo to afford 14.6 g of crude amide 6. A portion of the crude amide 6 (6.94 g, 17.9 mmol) was subdivided and dissolved in 50 mL of $CH_2Cl_2$ at 25° C. and 2-methoxypropene (3.43 mL, 35.8 mmol) was added followed by pyridinium paratoluenesulfonate (517 mg, 2.06 mmol) and the resulting solution was aged at 25° C. for 19 h. The reaction was quenched with 110 mL of saturated aqueous $NaHCO_3$ and the layers were separated, and the aqueous phase was back-extracted with $CH_2Cl_2$ (2×100 mL). The combined organic phase was washed with water (50 mL), dried with MgSO4 and concentrated in vacuo to afford 8.15 g of crude product that was dissolved in 50 mL of ethyl acetate and heated to reflux, then cooled to 25° C. and diluted with 100 mL of hexane while stirring over 1 h, then cooled to −20° C. and aged overnight. The resulting slurry was filtered and washed with cold (3:1) hexane/ethyl acetate and dried at high vacuum to afford 4.93 g of the acetonide amide derivative 7 as an off white solid. The compound 7 (2.76 g, 6.46 mmol) and triethylamine (940 μL, 6.7 mmol) were dissolved in 20 mL THF and 450 mg of 10% palladium on carbon was added. The resulting suspension was shaken on a paar shaker apparatus under 40 psi of hydrogen for 2.5 h, then filtered thru celite and concentrated in vacuo to afford 2.18 g of the phenol 8 as a foam.

$^{13}$C NMR (75.5 MHz, CDCl$_3$, major rotamer) δ$_c$ 170.0, 155.2, 140.6, 140.4, 131.7, 129.6, 128.6, 127.2, 125.8, 124.1, 115.5, 96.7, 78.7, 66.0, 38.8, 36.2, 31.4, 26.5, 24.0.

EXAMPLE 3

Preparation of morpholinoethyl amide 9

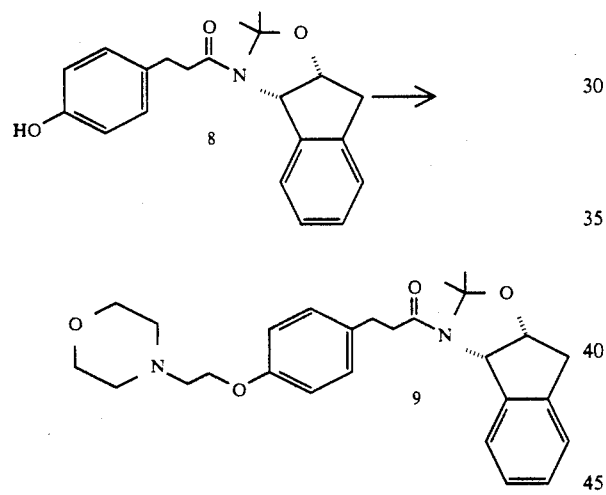

To a solution of crude phenol-amide 8 (2.18 g, 6.46 mmol) in 82 mL sieve dried CH$_3$CN at 25° C. was added powdered K$_2$CO$_3$ (2.23 g, 16.1 mmol) and N-(chloroethyl)morpholine hydrochloride (1.26 g, 6.77 mmol). The resulting slurry was heated to 80° C. and aged for 17 h. The mixture was then cooled to 25° C. and partitioned with 100 mL water and 200 mL ethyl acetate and the layers were separated. The aqueous layer was extracted with ethyl acetate (2×500 mL) and the combined organic layer was washed with saturated aqueous NaCl and dried over MgSO$_4$. The organic phase was concentrated in vacuo to afford 3.19 g of a crude product that was purified by chromatography on 160 g of silica gel. Elution with 5% methanol in ethyl acetate gave 2.80 g (94% from benzyl ether 7) of the desired morpholineothyl amide 9 as a gum.

$^{13}$C NMR (75.5 MHz, CDCl$_3$, major rotamer) δ$_c$ 168.9, 157.2, 140.8, 140.6, 133.2, 129.5, 128.4, 127.1, 125.8, 124.1, 114.6, 96.5, 78.6, 66.8, 65.9, 65.7, 57.6, 54.0, 38.6, 36.2, 31.0, 26.5, 24.1.

EXAMPLE 4

Preparation of epoxide 11

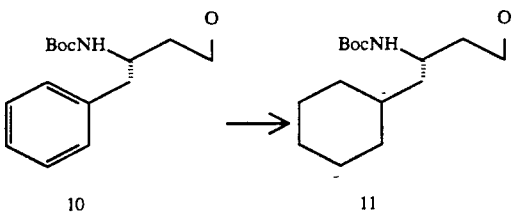

To a solution of epoxide 10 (1.00 g, 3.81 mmol) (prepared according to Luly, J. R., et al., *J. Org. Chem.* 1987, 52:1487) in 30 mL of ethyl alcohol at 25° C. was added 200 mg of 5% rhodium on alumina. The resulting mixture was hydrogenated in a shaker bomb at 25° C. at 500 psi for 22 h. The mixture was then filtered thru celite and concentrated in vacuo to afford a crude product that was purified by chromatography on 55 g of silica gel. Elution with hexanes/ethyl acetate (7:1) gave 981 mg (95%) of the cyclohexyl-epoxide 11 as a colorless oil.

$^{13}$C NMR (75.5 MHz, CDCl$_3$) δ$_c$ 155.7, 79.2, 54.0, 46.5, 44.4, 40.8, 34.1, 33.8, 32.8, 28.3, 26.5, 26.3, 26.1.

EXAMPLE 5

Preparation of isostere acetonide 12

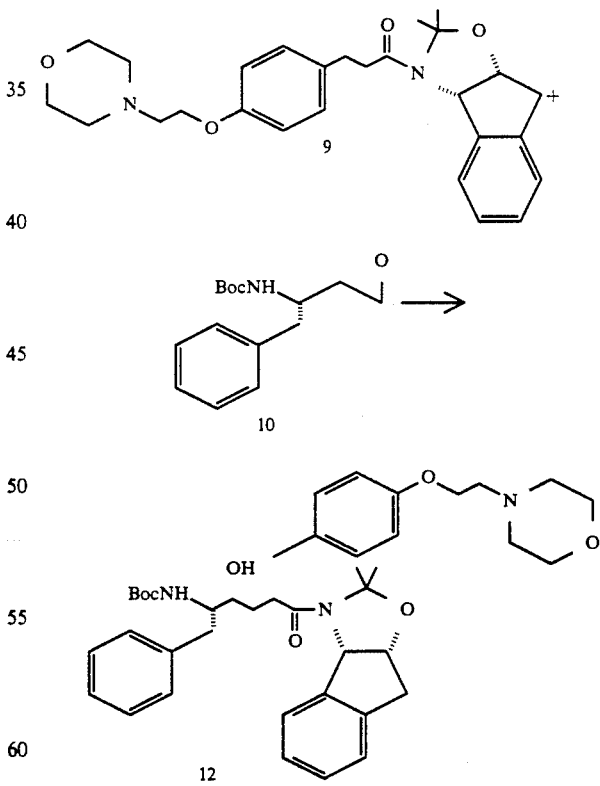

To a solution of the gummy amide 9 (902 mg, 2.00 mmol) in 10 mL sieve dried THF at −78° C. was added nBuLi in hexanes (1.25 mL, 2.00 mmol). The bright yellow solution was aged at −78° C. for 1 h. In a separate flask, a solution of isopropylmagnesium chloride (1.00 mL, 2.00 mmol) was added to a −78° C. solution of the epoxide 10 (527 mg, 2.00 mmol, 93:7 mixture (R:S) epoxides) in 8 mL sieve dried THF. After 15 min, the −78° C. epoxide solution was transferred via canula to the −78° C. amide enolate solution, then the mixture was warmed to −25° C. and aged for 3 h. The mixture was then warmed to 25° C. and aged for 13 h. The reaction was quenched with 25 mL water, and extracted with ethyl acetate (2×40 mL), washed with saturated aqueous sodium chloride (1×15 mL), dried (MgSO4) and concentrated in vacuo. Chromatography of the crude mixture on silica gel (80 g) eluting with 3% methanol in ethyl acetate gave 796 mg (60%) of the desired protected isostere acetonide 12 as a white foam.

$^{13}$C NMR (75.5 MHz, CDCl3, major rotamer) δ$_c$ 172.9, 157.5, 156.4, 140.6, 140.4, 138.2, 131.8, 130.3, 129.3, 128.5, 128.0, 126.9, 126.5, 125.5, 124.0, 114.6, 96.6, 79.6, 79.0, 67.8, 66.9, 65.7, 65.5, 57.6, 57.2, 54.0, 44.0, 38.2, 38.0, 37.2, 36.1, 28.3, 26.4, 23.9.

EXAMPLE 6

Preparation of hydroxy-amide 13

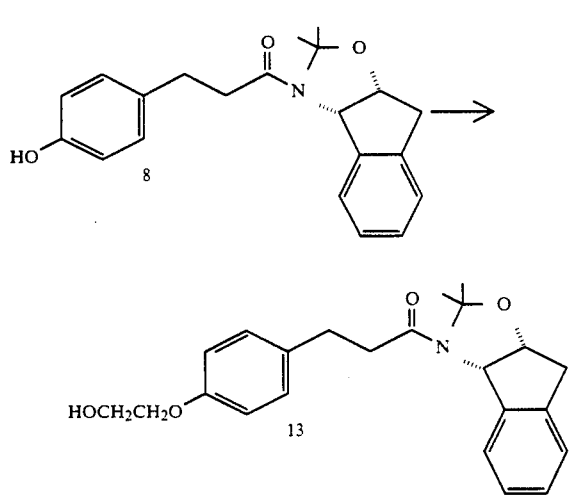

To a solution of the phenol 8 (1.86 g, 5.51 mmol) in 50 mL sieve dried acetonitrile at 25° C. was added powdered K2CO3 (916 mg, 6.63 mmol) followed by ethyl bromoacetate (673 μL, 6.07 mmol). The resulting mixture was aged for 2 days at 25° C. The suspension was filtered and the filter cake was washed with acetonitrile and the organic phase was concentrated in vacuo, and the residue was azeotroped with THF (2×50 mL) and dried at high vacuum. The residue was dissolved in 55 mL sieve dried THF at 25° C. and treated with 707 mg of LiBH4 (32.5 mmol). The resulting mixture was aged at 25° C. for 19 h and quenched with 20 mL of ethyl acetate at 25° C. The mixture was partitioned with 100 mL of ethyl acetate and 50 mL of water, the layers were separated and the aqueous layer was extracted with ethyl acetate (2×100 mL). The combined organic phase was washed with 50 mL water, 50 mL of saturated aqueous NaCl and dried over MgSO4. Removal of the volatiles in vacuo gave 2.2 g crude product that was purified by chromatography on 65 g of silica gel. Elution with hexanes/ethyl acetate (1:2) gave 2.07 g (98%) of the hydroxy-amide 13 as a white foam.

EXAMPLE 7

Preparation of Isostere acetonides 14, 15 and 16

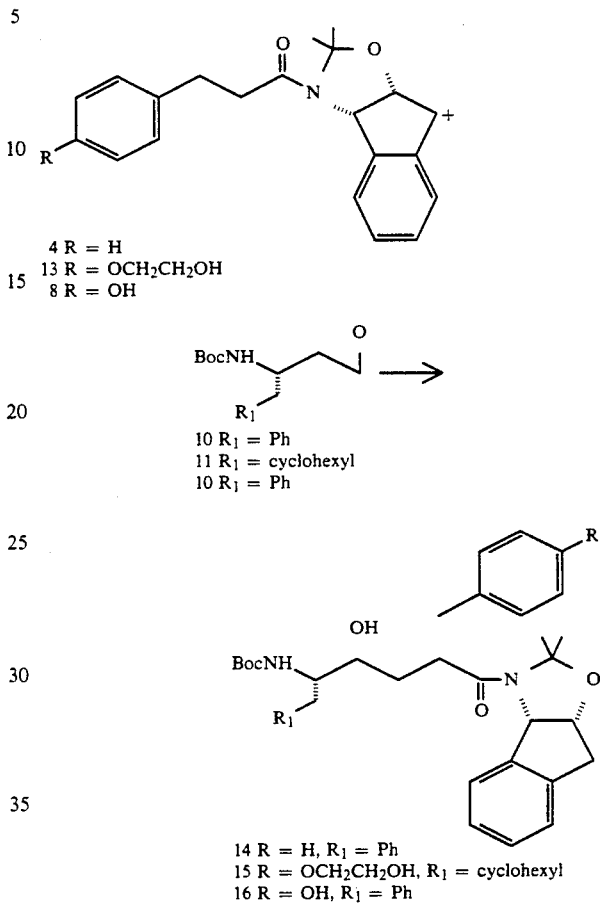

To a solution of epoxide 10 (159 mg, 0.604 mmol, 94:6 mixture of (R/S) epoxides) and amide 4 (194 mg, 0.604 mmol) in 4 mL sieve dried THF at −78° C. was added a solution of nBuLi in hexanes (760 μL, 1.21 mmol). The resulting yellow solution was aged at −78° C. for 1 h, then warmed to −25° C. and aged for 2 h. The reaction was quenched by addition of water (5 mL) at −20° C., and the mixture was extracted with ethyl acetate (2×40 mL). The combined ethyl acetate layer was washed with saturated sodium chloride, dried (MgSO4) and concentrated in vacuo. The crude product (365 mg) was purified by chromatography on 18 g silica gel eluting with hexanes/ethyl acetate (2:1 to 1:1) to afford 306 mg (92% based on (R)-epoxide) of the product 14. Trituration from hexanes/ethyl ether gave isostere acetonide 14 as a white solid.

$^{13}$C NMR (100.6 MHz, CDCl3, major rotamer) δ$_c$ 172.9, 156.5, 140.7, 140.4, 139.5, 138.3, 129.4, 128.7, 128.6, 128.1, 127.2, 126.7, 126.6, 125.6, 124.1, 96.7, 79.7, 79.1, 68.0, 65.7, 57.4, 43.9, 38.4, 38.2, 38.1$^5$, 36.2, 28.4, 26.5, 24.0.

To a solution of epoxide 10 (150 mg, 0.572 mmol 93:7 mixture of R/S epoxides) and amide 8 (194 mg, 0.575 mmol) in 2 mL of sieve dried THF at −78° C. was added nBuli in hexanes (1.09 mL, 1.73 mmol) while keeping the temperature below −69° C. After the nBuLi addition, 4 mL of THF was added to the thick slurry to facilitate stirring. The yellow slurry was aged at −78° C. for 1 h, −50° C. for 1 h, and −20° C. for 17 h. The thick mixture was quenched with 10 mL of water, extracted with ethyl acetate (2×30 mL) and the organic phase was washed with saturated aqueous NaCl, dried (MgSO$_4$) and concentrated in vacuo. The crude product was purified by chromatography on 17 g of silica gel. Elution with hexanes/ethyl acetate (2:1) gave 207 mg (65% based on (R) epoxide) of the isostere acetonide 16 as an oil.

$^{13}$C NMR (75.5 MHz, DMSO-d$_6$) δ$_c$ 173.3, 156.6, 155.2, 140.3, 140.2, 138.1, 130.7, 130.4, 129.3, 128.5, 128.1, 127.0, 126.5, 125.5, 124.1, 115.6, 96.7, 79.9, 79.1, 68.2, 65.6, 57.2, 44.1, 38.1, 37.7, 37.4, 36.0, 28.2, 26.4, 23.9.

Use of the above procedure with epoxide 11 (512 mg, 1.90 mmol) and amide 13 (740 mg, 1.94 mmol) gave after purification by chromatography on 72 g of silica gel and elution with hexanes/ethyl acetate (1:1), 655 mg (53%) of the isostere acetonide 15 as a solid foam.

$^{13}$C NMR (75.5 MHz, CDCl$_3$, major rotamer) δ$_c$ 172.9, 157.6, 156.7, 140.8, 140.4, 132.4, 130.6, 128.1, 126.9, 125.6, 124.2, 114.7, 96.7, 79.6, 79.2, 70.9, 69.3, 65.7, 61.4, 53.3, 44.1, 39.2, 38.4, 37.9, 36.2, 34.4, 33.8, 32.9, 28.4, 26.6, 26.4, 26.2, 24.1.

EXAMPLE 8

Preparation of isosteres 17, 18, 19 and 20

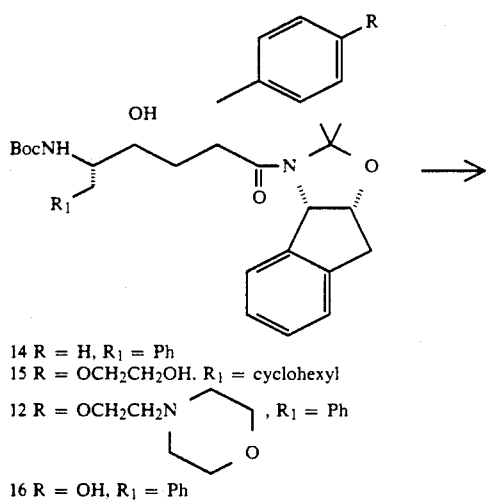

14 R = H, R$_1$ = Ph
15 R = OCH$_2$CH$_2$OH, R$_1$ = cyclohexyl
12 R = OCH$_2$CH$_2$N(CH$_2$CH$_2$)$_2$O, R$_1$ = Ph
16 R = OH, R$_1$ = Ph

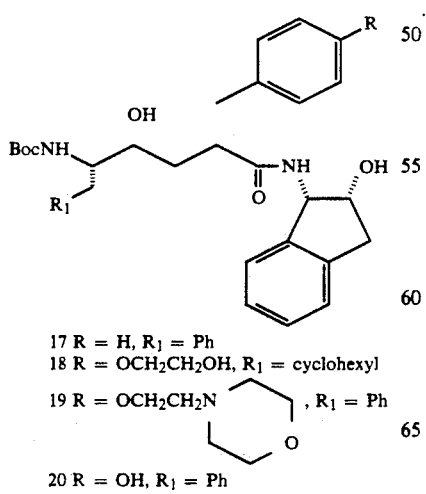

17 R = H, R$_1$ = Ph
18 R = OCH$_2$CH$_2$OH, R$_1$ = cyclohexyl
19 R = OCH$_2$CH$_2$N(CH$_2$CH$_2$)$_2$O, R$_1$ = Ph
20 R = OH, R$_1$ = Ph To a solution of the crude acetonide derivative 14 (2.00 g, 3.42 mmol) in 10 mL methanol at 0° C. was added camphorsulfonic acid (200 mg, 0.86 mmol) followed by ethylene glycol (382 μL, 6.8 mmol). The mixture was warmed to 25° C. and aged for 24 h (15 mL of methanol was added to the thick slurry after 2 h to facilitate stirring). The slurry was cooled to 0° C., filtered thru a sintered glass funnel, and washed with 10 mL of cold methanol, and dried at high vacuum to afford 1.20 g (75% overall form (R)-epoxide) of the isostere 17 (Vacca, et al., *J. Med. Chem.* 1991, 34: 1228) as a white solid.

$^{13}$C NMR (75.5 MHz, DMSO-d$_6$) δ$_c$ 174.6, 155.3, 142.2, 140.6, 140.0, 139.7, 129.0, 128.9, 128.0, 127.9, 127.0, 126.1, 125.8, 125.7, 124.7, 124.1, 77.3, 72.1, 68.9, 56.6, 56.3, 43.8, 39.7, 38.9, 35.7, 35.4, 28.2.

Use of the above procedure with acetonide derivative 15 (2.13 g, 3.27 mmol) gave 1.21 g (61%) of the deblocked isostere 18 as a powdery solid.

$^{13}$C NMR (75.5 MHz, DMSO-d$_6$) δ$_c$ 174.8, 156.8, 155.5, 142.3, 140.6, 131.8, 129.7, 127.0, 126.0, 124.7, 124.0, 114.0, 77.2, 72.1, 69.7, 69.3, 59.5, 56.6, 51.8, 44.0, 39.8, 38.0, 37.7, 35.7, 33.8, 33.4, 32.1, 28.2, 26.1, 25.9, 25.8.

Use of the above procedure with acetonide derivative 12 (31 mg, 0.043 mmol) gave 17.5 mg (60%) of the deblocked isostere 19 as a white solid.

$^{13}$C NMR (75.5 MHz, DMSO-d$_6$) δ$_c$ 174.8, 156.7, 155.4, 142.2, 140.6, 139.7, 131.9, 129.8, 129.0, 128.0, 127.1, 126.2, 125.7, 124.7, 124.2, 114.1, 77.4, 72.2, 68.9, 66.2, 65.2, 57.1, 56.7, 56.3, 53.6, 44.1, 39.8, 38.1, 35.8, 35.3, 28.2.

Use of the above procedure with acetonide derivative 16 gave the deblocked isostere 20.

What is claimed is:

1. A process for making a compound of structural formula:

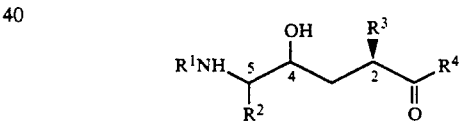

which consists essentially of reacting an epoxide of formula:

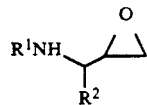

with about one equivalent of an amide of structural formula:

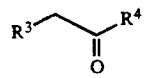

by treatment with a strong base at low temperatures wherein:

R$^1$ is:
   a) t-Boc, Aoc, Adc, Mcb, Mch, Cbz, Alloc, or Fmoc,
   b) benzyl,
   c) lower alkyl, d) $CH_3O(CH_2CH_2O)_nCO—$, wherein n is from 1 to 10,
e) tetrahydrofuranyloxy—CO—, or
f) R—CO—, wherein R is an amino acid;

$R^2$ is:
a) —H
b) benzyl,
c) cyclohexyl—$CH_2$—,
d) isobutyl,
e) benzyl—O—benzyl—,
f) cinnamyl—, or
f) parahydroxybenzyl;

$R^3$ is:
a) hydrogen,
b) lower alkyl,
c) phenyl
d) benzyl,
e) —$CH_2$—phenyl—O—$R^5$, or
f) —$CH_2$—CH=CH—phenyl—O—$R^5$;

$R^4$ is:
a)

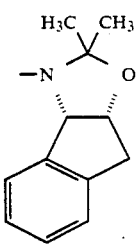

b)

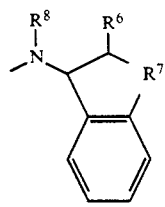

wherein:
$R^6$ is —$H_4$ or —OH;
$R^7$ is —$CH_2$—O—, or

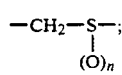

n=0, 1, or 2;

c)

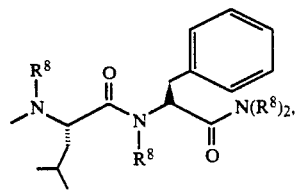

d)

e)

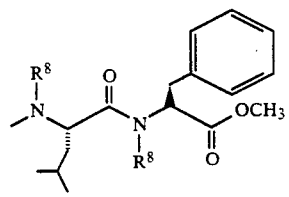

f)

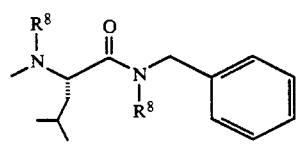

g)

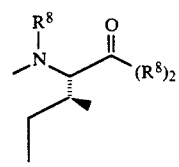

or h)

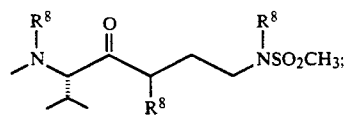

$R^5$ is:
a) —H
b) benzyl,
c) —$CH_2CH_2$—OH, or
d)

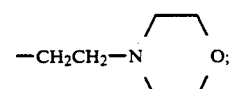

$R^8$ is a removable protecting group selected from among:
a) t-Boc, Aoc, Adc, Mcb, Mch, Cbz, Alloc, or Fmoc, or
b) benzyl; and $R^9$ is:
a) lower alkyl, or
b) benzyl.

2. The process of claim 1 wherein:
$R^1$ is t-Boc, Aoc, Adc, Mcb, Mch, Cbz, Alloc, or Fmoc;

R² is —H, benzyl, cyclohexyl—CH₂—, or parahydroxybenzyl;

R³ is pheny, benzyl, or —CH₂—phenyl—O—R⁵; and the strong base is chosen from the group consisting of n-butyllithium, s-butyllithium, t-butyllithium, potassium tert-butoxide, lithium diisopropylamide, lithium isopropylcyclohexylamide, lithium pyrrolidide, lithium tetramethylpiperidide, phenyllithium, isopropylmagnesium chloride, and isobutylmagnesium chloride.

3. The process of claim 1 for making a compound of strucural formula:

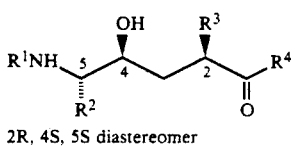

2R, 4S, 5S diastereomer which comprises reacting an epoxide of formula:

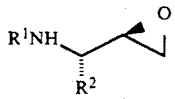

with about one equivalent of an amide of formula:

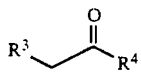

4. The process of claim 3 wherein:

R¹ is t-Boc, Aoc, Adc, Mcb, Mch, Cbz, Alloc, or Fmoc;

R² is —H, benzyl, cyclohexyl—CH₂—, or parahydroxybenzyl;

R³ is phenyl, benzyl, or —CH₂—phenyl—O—R⁵; and

R⁴ is

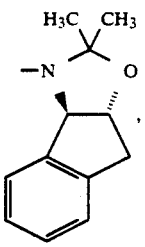

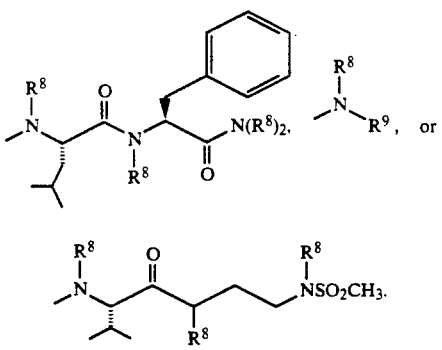

5. The process of claim 4 wherein the strong base is chosen from the group consisting of n-butyllithium, s-butyllithium, lithium diisopropylamide and isopropylmagnesium chloride.

6. The process of claim 5 wherein the low temperature is in the range of about −82° C. to −65° C. to effect metalation of the amide and the epoxide, and the temperature is in the range of about −50° C. to −10° C. to effect the reaction of the metalated derivatives of the amide and the epoxide.

7. The process of claim 6 wherein:

R¹ is t-Boc;

R² is benzyl or cyclohexyl—CH₂—;

R³ is benzyl or —CH₂—phenyl—O—R⁵;

R⁴ is:

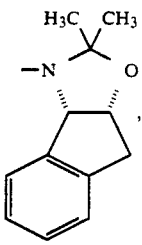

and

R⁵ is —H, —CH₂CH₂—OH, or

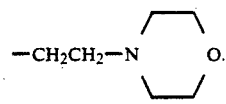

8. The process of claim 7 wherein the strong bases are chosen from the group consisting of n-butyllithium and isopropylmagnesium chloride.

9. The process of claim 7 wherein the temperature is in the range of about −80° C. to −75° C. to effect metalation of the amide and the epoxide, and the temperature is in the range of about −30° C. to −20° C. to effect the reaction of the metalated derivatives of the amide and the epoxide.

10. The process of claim 7 wherein R⁴ is deprotected to the free amino alcohol.

* * * * *